(12) United States Patent
Venkat et al.

(10) Patent No.: US 11,803,252 B2
(45) Date of Patent: Oct. 31, 2023

(54) AUTOMATED WORKFLOW ACCESS BASED ON CLINICAL USER ROLE AND LOCATION

(71) Applicant: CERNER INNOVATION, INC., Kansas City, KS (US)

(72) Inventors: Chandrasekhar Kaiwar Venkat, Leawood, KS (US); Jennifer Montag, Kansas City, MO (US); Abhishek Parajuli, Kansas City, MO (US); Stuart Jackson, Kansas City, MO (US)

(73) Assignee: CERNER INNOVATION, INC., Kansas City, MO (US)

( * ) Notice: Subject to any disclaimer, the term of this patent is extended or adjusted under 35 U.S.C. 154(b) by 0 days.

(21) Appl. No.: 17/530,839

(22) Filed: Nov. 19, 2021

(65) Prior Publication Data
US 2022/0075455 A1    Mar. 10, 2022

Related U.S. Application Data

(63) Continuation of application No. 15/836,554, filed on Dec. 8, 2017, now Pat. No. 11,231,788, which is a continuation of application No. 13/629,983, filed on Sep. 28, 2012, now Pat. No. 9,858,630.

(51) Int. Cl.
*G16H 10/60* (2018.01)
*G16H 40/20* (2018.01)
*G06F 3/023* (2006.01)
*A61B 34/10* (2016.01)
*G16Z 99/00* (2019.01)

(52) U.S. Cl.
CPC ............ *G06F 3/0233* (2013.01); *A61B 34/10* (2016.02); *G16H 10/60* (2018.01); *G16H 40/20* (2018.01); *G16Z 99/00* (2019.02)

(58) Field of Classification Search
CPC ....... G06F 3/0233; G16H 10/60; G16H 40/20
See application file for complete search history.

(56) References Cited

U.S. PATENT DOCUMENTS

| 7,676,380 | B2 | 3/2010 | Graves et al. |
| 7,707,044 | B2 | 4/2010 | Graves et al. |
| 8,127,001 | B1 | 2/2012 | Sylvain |
| 8,346,572 | B2 | 1/2013 | Eaton et al. |
| 8,508,336 | B2 | 8/2013 | Giobbi et al. |
| 9,858,630 | B2 | 1/2018 | Venkat et al. |
| 2006/0185005 | A1* | 8/2006 | Graves ............... G16Z 99/00 707/E17.001 |

(Continued)

FOREIGN PATENT DOCUMENTS

WO    WO-2012144970 A1 *  10/2012  ............. G06F 21/60

*Primary Examiner* — Sheetal R Paulson
(74) *Attorney, Agent, or Firm* — KRAGULJAC LAW GROUP, LLC

(57) ABSTRACT

Systems, methods, computer-readable media for automating displays based on admissions, transfers, and discharges are provided. In embodiments, a location associated with a clinician is detected. A role associated with the clinician authenticated to a first device is determined. One or more applications associated with the clinician based on the location and the role is automatically launched on the first device. In embodiments, authentication requests from the clinician are received for a second device. A session associated with the one or more applications is suspended on the first device and resumed on the second device.

20 Claims, 3 Drawing Sheets

(56) References Cited

U.S. PATENT DOCUMENTS

| | | | |
|---|---|---|---|
| 2006/0288095 A1* | 12/2006 | Torok | G16H 40/20 709/223 |
| 2007/0234048 A1 | 10/2007 | Ziv | |
| 2009/0182577 A1 | 7/2009 | Squilla et al. | |
| 2009/0206992 A1 | 8/2009 | Giobbi et al. | |
| 2010/0138231 A1 | 6/2010 | Linthicum et al. | |
| 2011/0106560 A1 | 5/2011 | Eaton et al. | |
| 2011/0295616 A1 | 12/2011 | Vesto | |
| 2012/0095779 A1* | 4/2012 | Wengrovitz | G16H 10/60 705/3 |
| 2012/0173635 A1* | 7/2012 | Wormald | G06Q 10/107 709/206 |
| 2013/0173291 A1* | 7/2013 | Kelly | G16H 15/00 705/3 |
| 2013/0185772 A1* | 7/2013 | Jaudon | H04L 63/08 726/4 |
| 2013/0243275 A1 | 9/2013 | Baym et al. | |
| 2013/0260794 A1 | 10/2013 | Prchal et al. | |
| 2014/0095180 A1 | 4/2014 | Venkat et al. | |
| 2016/0027138 A1* | 1/2016 | Larsen | G06F 21/31 705/2 |
| 2018/0101922 A1 | 4/2018 | Venkat et al. | |

\* cited by examiner

AUTOMATED WORKFLOW ACCESS BASED ON CLINICAL USER ROLE AND LOCATION

CROSS-REFERENCE TO RELATED APPLICATION

This application is a continuation of U.S. Nonprovisional patent application Ser. No. 15/836,554, entitled "Automatic Workflow Access Based On User Role And Location" and filed on Dec. 8, 2017, which is a continuation of U.S. Pat. No. 9,858,630, entitled "Automatic Workflow Access Based On User Role And Location" and filed Sep. 28, 2012, which are incorporated by reference herein, in their entireties.

BACKGROUND

Patient medical information, such as that contained in a medical record, allows health care providers to provide continuity of care to patients. It is critical for clinicians providing care to patients to review and update each patient's medical record. The growth in access to and utilization of electronic medical records by healthcare providers and facilities has significantly reduced the time and organization efforts required by paper medical records. Unfortunately, this growth has introduced new problems. Medical records associated with the incorrect patient are often mistakenly viewed without knowledge by the clinician.

Exacerbating this problem further, clinicians are constantly on the move. For example, clinicians are responsible for patients in multiple healthcare facilities or multiple areas within a single healthcare facility. Each area or each facility may have different software applications or different components within an application supporting various aspects of the clinicians working in those areas or facilities. While making rounds, clinicians are constantly required to login to different devices and applications or change views from within an application to perform their duties. Time spent logging into applications, navigating to the appropriate view or area within an application, and then locating the correct records can adversely impact any efficiency gained by utilizing electronic medical records.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention relate to methods, systems, and computer readable media for automating workflows based on user roles and locations. Accordingly, in one embodiment, computer storage media having computer-executable instructions embodied thereon that, when executed, facilitate a method of automating workflow access based on user role and location. A location associated with a clinician in a healthcare facility is detected. A role associated with the clinician authenticated with a first device is determined. One or more applications associated with the clinician based on the location and the role is automatically launched on the first device.

In another embodiment, a computer system, comprising a processor coupled to a computer storage medium, the computer storage medium having stored thereon a plurality of computer software components executable by the processor, for automating workflows based on user roles and locations is provided. A detecting component detects a location associated with a clinician in a healthcare facility. A role component determines a role associated with the clinician authenticated with a first device. An application component launches, on the first device, one or more applications associated with the clinician based on the location and the role. A session component suspends a session associated with the one or more applications on a first device and resumes the session associated with the one or more applications on a second device when the clinician logs into the second device.

In one embodiment, computer storage media having computer-executable instructions embodied thereon that, when executed, facilitate a method of automating workflow access based on user role and location. A role associated with a clinician authenticated to a first device is communicated from the first device. A workplace including one or more applications associated with the clinician and based on the location and the role of the clinician is received from a server. The workplace is displayed on the first device.

BRIEF DESCRIPTION OF THE DRAWINGS

Embodiments are described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies.

Having briefly described embodiments of the present invention, an exemplary operating environment suitable for use in implementing embodiments of the present invention is described below.

Figure 1:
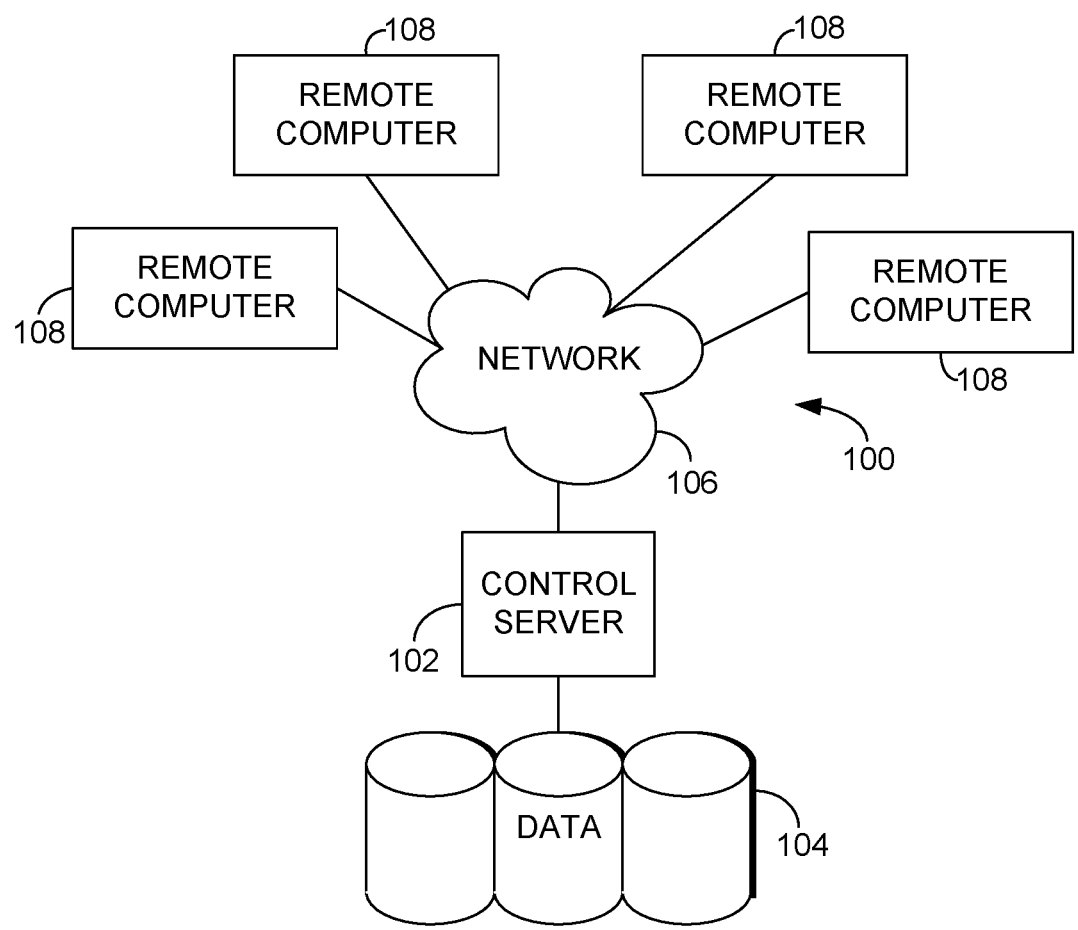
FIG. 1 is a block diagram of an exemplary computing environment suitable for use in implementing embodiments of the present invention.

Referring to the drawings in general, and initially to FIG. 1 in particular, an exemplary computing system environment, a medical information computing system environment, with which embodiments of the present invention may be implemented is illustrated and designated generally as reference numeral 100. It will be understood and appreciated by those of ordinary skill in the art that the illustrated medical information computing system environment 100 is merely an example of one suitable computing environment and is not intended to suggest any limitation as to the scope of use or functionality of the invention. Neither should the medical information computing system environment 100 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in association with local and/or remote computer storage media including, by way of example only, memory storage devices.

With continued reference to FIG. 1, the exemplary medical information computing system environment 100 includes a general purpose computing device in the form of a control server 102. Components of the control server 102 may include, without limitation, a processing unit, internal system memory, and a suitable system bus for coupling various system components, including database cluster 104, with the control server 102. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of computer-readable media, for instance, database cluster 104. Computer-readable media can be any available media that may be accessed by server 102, and includes volatile and nonvolatile media, as well as removable and non-removable media. By way of example, and not limitation, computer-readable media may include computer storage media. Computer storage media may include, without limitation, volatile and nonvolatile media, as well as removable and non-removable media implemented in any method or technology for storage of information, such as computer-readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 102. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer storage media discussed above and illustrated in FIG. 1, including database cluster 104, provide storage of computer-readable instructions, data structures, program modules, and other data for the control server 102. The control server 102 may operate in a computer network 106 using logical connections to one or more remote computers 108. Remote computers 108 may be located at a variety of locations in a medical or research environment, for example, but not limited to, clinical laboratories (e.g., molecular diagnostic laboratories), hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as intensivists, surgeons, radiologists, cardiologists, and oncologists, emergency medical technicians, physicians' assistants, nurse practitioners, nurses, nurses' aides, pharmacists, dieticians, microbiologists, laboratory experts, laboratory technologists, genetic counselors, researchers, veterinarians, students, and the like. The remote computers 108 may also be physically located in non-traditional medical care environments so that the entire health care community may be capable of integration on the network. The remote computers 108 may be personal computers, servers, routers, network PCs, peer devices, other common network nodes, or the like, and may include some or all of the elements described above in relation to the control server 102. The devices can be personal digital assistants or other like devices.

Exemplary computer networks 106 may include, without limitation, local area networks (LANs) and/or wide area networks (WANs). Such networking environments are commonplace in offices, enterprise-wide computer networks, intranets, and the Internet. When utilized in a WAN networking environment, the control server 102 may include a modem or other means for establishing communications over the WAN, such as the Internet. In a networked environment, program modules or portions thereof may be stored in association with the control server 102, the database cluster 104, or any of the remote computers 108. For example, and not by way of limitation, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) may be utilized.

In operation, a clinician may enter commands and information into the control server 102 or convey the commands and information to the control server 102 via one or more of the remote computers 108 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the control server 102. These commands and information may include input or a trigger (i.e., a user moving from one location to another) from a real-time location system, such as detection component described herein. In addition to a monitor, the control server 102 and/or remote computers 108 may include other peripheral output devices, such as speakers and a printer.

Although many other internal components of the control server 102 and the remote computers 108 are not shown, those of ordinary skill in the art will appreciate that such components and their interconnection are well known.

Accordingly, additional details concerning the internal construction of the control server 102 and the remote computers 108 are not further disclosed herein.

Figure 2:
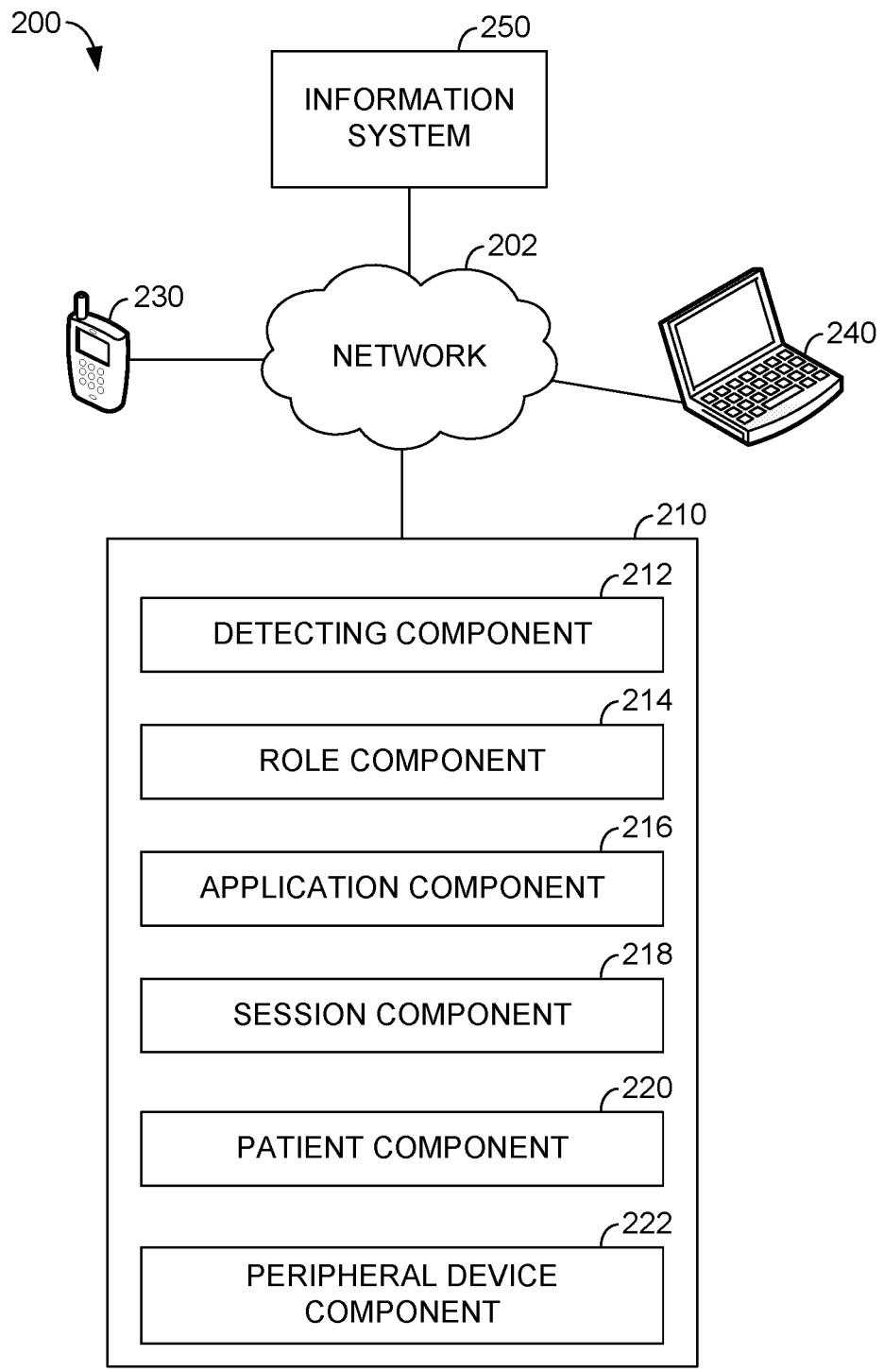
FIG. 2 is an exemplary system architecture suitable for use in implementing embodiments of the present invention.

With reference to FIG. 2, a block diagram is illustrated that shows an exemplary computing system architecture 200 for automating workflows based on user role and location. It will be appreciated that the computing system architecture 200 shown in FIG. 2 is merely an example of one suitable computing system and is not intended as having any dependency or requirement related to any single module/component or combination of modules/components.

The computing system 200 includes network 202, automated workflow module 210, mobile device 230, workstation 240, and information system 250. Although only single instances of the elements are depicted in computing system 200, it should be appreciated the many instances of each of the elements are contemplated and within the scope of the invention. For example, many mobile devices or workstations can be in communication with automated workflow module 210. Similarly, many information systems associated with any number of applications may be in communication with automated workflow module 210. Applications hosted by information system 250 include any application that may be utilized by a clinician. For example, information system 250 may include applications supporting email, messaging, browsing, research, electronic medical records, imaging, any healthcare related function, and the like. Information system 250 may also include applications supporting admission, discharge, and transfer systems. Information system 250 may further include applications supporting location, tracking, and proximity detection.

Automated workflow module 210 may reside on one or more computing devices, such as, for example, the control server 102 described above with reference to FIG. 1. By way of example, the control server 102 includes a computer processor and may be a server, personal computer, desktop computer, laptop computer, handheld device, mobile device, consumer electronic device, or the like. Automated workflow module 210 comprises, in various embodiments, detecting component 212, role component 214, application component 216, session component 218, patient component 220, and peripheral device component.

Detection component 212 detects a location associated with a clinician in a healthcare facility. In one embodiment, detection component 212 detects location changes associated with the clinician. In one embodiment, detection component 212 receives location information from a clinician tracking system. For example, healthcare resources such as clinicians, patients, equipment, clinical devices, and the like may be tracked via a plurality of sensors in the healthcare environment. The sensors in the healthcare environment may utilize ultrasound technology, infrared technology, radio-frequency identification technology, near field communication (NFC), and the like. Using said technology, the sensors send out signals to clinician identifiers, patient identifiers, item identifiers, clinical device identifiers, or the like. An exemplary sensor system is the Cricket Indoor Location System sponsored by the MIT Project Oxygen partnership.

The signals are received by the identifiers and the identifiers respond to the signals. A response from an identifier is received by the sensors and the sensors are able to recognize and determine the location of the responding identifier and, thus, are aware of the resources within the healthcare environment. The respective identifiers associated with the resources may be located, e.g., on the person, on the item, or on the device. Exemplary identifiers include badges, wristbands, tags, passive location sensors, and the like. The locations of clinicians, patients, equipment, or the like, associated with a responding identifier, is presented or displayed on the dashboard.

In one embodiment, detection component 212 detects a location associated with the clinician by associating a device the clinician is logged into with the clinician's location. The clinician may log-in to the device in any number of ways, such as by physically entering log-in credentials or scanning credentials associated with a badge into an input device or touchscreen associated with the device. Or, the clinician may log-in to the device by proximity detection, such as with a badge.

Once the clinician has logged into automated workflow module 210 in any of the ways described above, role component 214 determines a role associated with the clinician authenticated with a first device. The role may be determined by roles or rights assigned to the clinician's login credentials or to a position or title associated with the clinician. The role may further be influenced by a location of the clinician. The location may be a particular area of a single healthcare facility or may be a particular healthcare facility among a plurality of healthcare facilities. For example, a clinician may have different roles depending on the particular unit within the healthcare facility the clinician is located. Or, the clinician may have different roles depending on the particular healthcare facility (that may be part of a related or commonly managed network of healthcare facilities) a clinician is making rounds.

Application component 216 launches, on the first device, one or more applications associated with the clinician based on the location and the role. In one embodiment, the applications are part of a workspace associated with the clinician. In one embodiment, the applications include a patient list for a particular location to assist the clinician working in that location. In one embodiment, application component 216 launches one or more clinical applications when detecting component 212 detects the clinician's location is a patient-specific location. For example, when the clinician is in a patient-specific location (e.g., a patient's room), the clinician does not need access to all of the applications associated with the clinician's workspace. Rather than launching non-clinical applications such as applications supporting email, messaging, or browsing, application component 216 only launches clinical applications that are relevant to perform the clinician's duties in that location for the role associated with the clinician as determined by role component 214. In another embodiment, application component 216 automatically opens an appropriate application or record within an application. For example, when the clinician enters a patient's room, if the clinician does not already have the patient's EMR open or even an EMR application open, application component 216 automatically opens the EMR for that particular patient. In this sense, the application state reflects the appropriate changes due to a change in location, while preserving the application's current session information.

In another embodiment, application component 216 launches one or more non-clinical applications when detecting component 212 detects the clinician is in a location where the privacy of a patient or group of patients may be violated. In another embodiment, application component 216 masks identifying data associated with one or more clinical applications so the clinician can continue working with a particular clinician application even when the clinician is not in a patient-specific location or if the clinician is in a location where the privacy of a patient or group of patients may be violated. For example, a clinician may desire to view or chart within a particular patient's record while the clinician is outside the patient's room (e.g., at a nurse's station, a shared device, or on a mobile device). In order to not reveal the patient's identity to someone who may be passing by, detecting component 212 detects the clinician is not inside the patient's room or in the clinician's private office and masks, partially masks, hides, obscures, or otherwise removes any identifying information.

Session component 218 suspends a session associated with the one or more applications on a first device and resumes the session associated with the one or more applications on a second device when the clinician logs into or authenticates with the second device. For example, as a clinician walks into a patient's room, the clinician may be reviewing, on a mobile device, a record associated with the patient (e.g., patient's electronic medical record (EMR), laboratory results, image, etc.). Once the clinician is inside the patient's room, the clinician may desire to log into or authenticate with a workstation or other device in the patient's room. As the clinician logs into or authenticates with that workstation or other device, session component suspends the session on the mobile device and then resumes the session on the workstation or other device. For clarity, the session refers to a state within a particular application. For example, the clinician above may have a particular application open on the clinician's mobile device. The clinician may have even navigated to a particular item or view within that application. Rather than simply closing the application on the mobile device and reopening the application on the workstation or other device (or closing the application on the mobile device and then having to reopening the application within the clinician's workspace) and then navigating to that particular item or view, session component 218 allows the clinician to essentially pick up where that clinician left off within that application while on the mobile device.

In one embodiment, session component 218 suspends a session with the one or more applications on a first device and resumes the session on a second device with one or more applications associated with the second device. In other words, session component 218 resumes the session for the clinician on the second device but only with applications appropriate for the second device or a location associated with the second device. Applications which are not included in the resumed session on the first device are suspended until the clinician logs into another device or is in a location where those applications are needed.

In one embodiment, session component 218 suspends a session on a first device utilizing at least one first device native application and resumes the session on a second device utilizing at least one second device native application. For example, a clinician may be accessing a patient's chart on a session on a first device. The first device may be an iPad and the chart may be opened on a native iOS application. If the clinician log into a second device in the patient's room that is running another operating system, such as a version of Microsoft Windows, the session is suspended on the first device and resumed on the second device, but with the patient's chart opened in a Microsoft Windows® based EMR application to enable a smooth workflow for the clinician.

In one embodiment, patient component 220 detects a patient associated with the location. Patient component 220 may receive patient location information from an admission, discharge, and transfer system that associates a patient with a location based on admissions, discharges, and transfers. Or, patient component 220 may receive patient location from a tracking system such as the one described herein with respect to detecting component 212.

In one embodiment, peripheral device component 222 automatically populates a list of available peripheral devices associated with the second device. For example, an application may include a print function or some other function that requires the use of a peripheral device. The peripheral device may be directly connected to the second device or connected via a network. Each device within a healthcare facility may be associated with different peripheral devices depending on a location within the healthcare facility. Rather than a clinician's session resuming on a second device with peripheral device information from a previous device, peripheral device component 222 automatically updates the resumed session (and each application included therein) with the peripheral device information that is normally associated with the second device. This allows, for example, the clinician to print an image or other information to the printer normally utilized by the second device without having to manually configure or select the appropriate printer.

Figure 3:
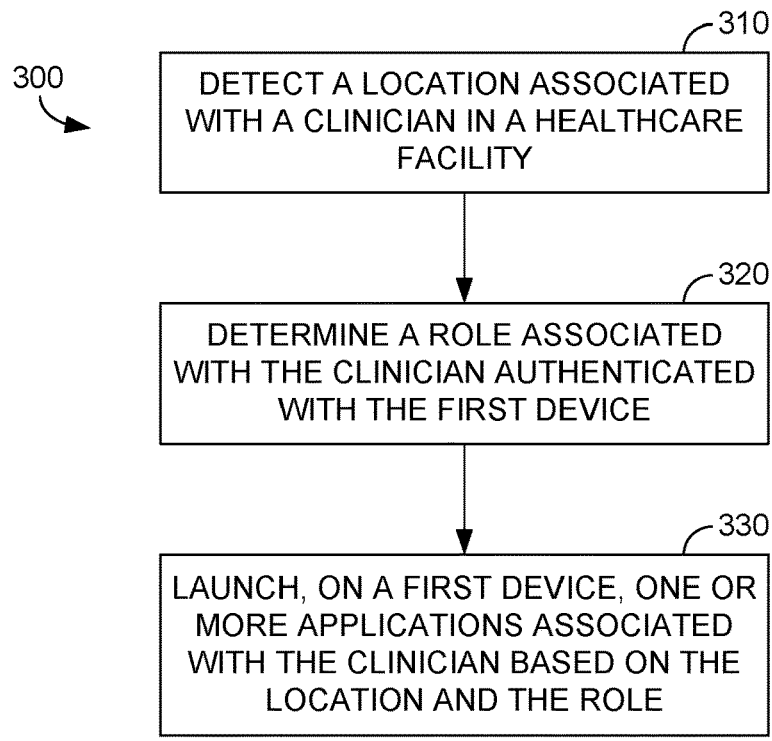
FIGS. 3-4 are flow diagrams of methods in accordance with embodiments of the present invention.

Referring now to FIG. 3, a flow diagram depicts an illustrative method 300 of automating workflow access based on user role and location, in accordance with an embodiment of the present invention. Initially, at step 310 a location associated with a clinician in a healthcare facility is detected. A role associated with the clinician authenticated with a first device is determined at step 320. One or more applications associated with the clinician based on the location and the role is automatically launched, at step 330, on the first device.

In one embodiment, the location is a non-patient-specific location. For example, the location may be an office associated with the clinician, a shared workstation utilized by clinical staff, a mobile device, and the like. In this example, a clinician may desire to access applications unrelated to a patient. In one embodiment, the one or more applications are non-clinical applications associated with the location. For example, the clinician may desire access to email, messaging, browser applications, and the like. When a non-patient-specific location is detected, these non-clinical applications may be included in a workspace associated with the clinician. Further, depending on the particular non-patient-specific location, clinical applications may or may not be included in the clinician's workspace. For example, a clinician may desire to work on clinical applications while in the clinician's office, but due to privacy concerns may not desire to work on clinical applications while on a shared device, in an area accessible to non-medical personnel or non-healthcare facility staff, or on a mobile device. In some of these instances, the clinician may desire to work on clinical applications, but only if patient identifying data is hidden or masked as described above. In various embodiments, the type of applications included in the clinician's workspace is determined by a location and a role associated with a clinician, as well as preferences of the clinician or protocols defined by the particular healthcare facility or as otherwise required.

In one embodiment, the location is a patient-specific location. The patient-specific location may include a patient's room. In one embodiment, the one or more applications are clinical applications associated with the patient-specific location. For example, the applications included in a clinician's workspace when a patient-specific location is detected may include applications related to patient care, such as applications associated with a patient's EMR. Further, the clinician may not have a need for non-clinical applications and these may be excluded from the clinician's workspace in this context.

In one embodiment, an authentication request is received from the clinician for a second device in the healthcare facility. For example, the clinician may be utilizing a mobile device while making rounds. As the clinician enters a patient's room, the clinician may log into or authenticate with a second device, such as an anchor device that is associated with the patient's room. In a another example, the clinician may currently be authenticated with an anchor device in a patient's room, and as the clinician leaves the patient's room, the clinician is automatically logged out of the anchor device and reauthenticated with the mobile device. Similarly, the clinician may encounter a shared workstation, such as at a nurse's station, or a workstation in the clinician's office. The clinician may login to or authenticate with one of those devices.

In one embodiment, after the authentication request is received for the second device, a session associated with the one or more applications on the first device is suspended. As described above, the session refers to a state of or a placeholder within an application. For example, if a clinician is working within a particular application (e.g., editing data within a particular field of a patient's EMR or viewing a particular area of an image), when the authentication request is received for the second device, that particular state of the application (i.e., the session) is suspended. In one embodiment, the session associated with the one or more applications is resumed on the second device. Whatever state the application or applications were in on the first device are automatically resumed on the second device as if the clinician never switched devices. So, if the clinician were updating a particular field of a patient's EMR or viewing a particular area of an image when the clinician authenticates with the second device, the state of those applications are resumed on the second device so the clinician can continue updating that particular field of the patient's EMR or viewing that particular area of the image. In other words, the clinician's workspace opens up in the same state, at the same point within an application or applications as it was on the first device (except for peripheral device information which, in one embodiment, is automatically updated to include the appropriate peripheral device information for the second device).

Figure 4:
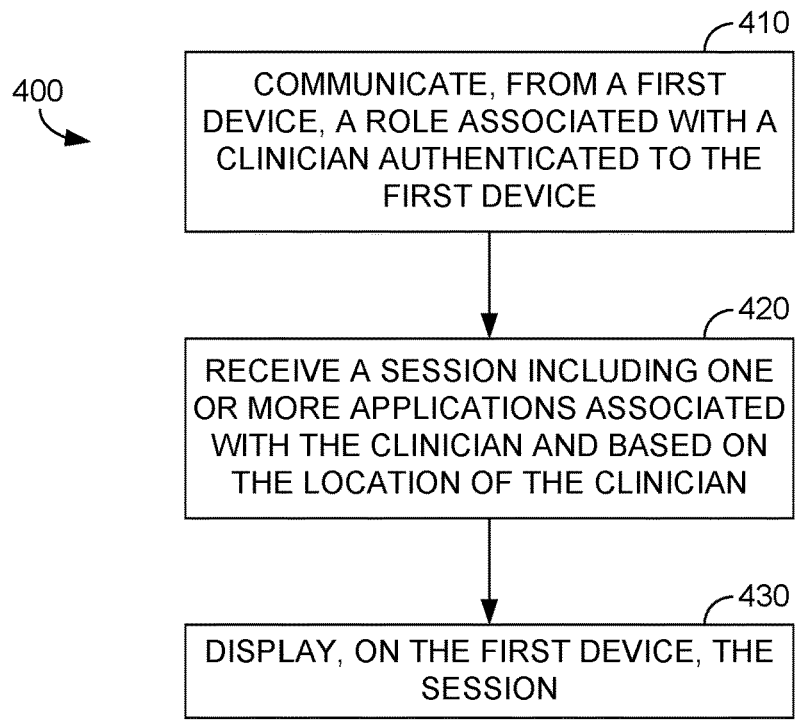

Referring now to FIG. 4, a flow diagram depicts an illustrative method 400 of automating workflow access based on user role and location, in accordance with an embodiment of the present invention. Initially, at step 410, a role associated with a clinician authenticated to a first device is communicated from the first device. The role may be determined by roles or rights assigned to the clinician's login credentials or to a position or title associated with the clinician. The role may further be influenced by a location of the clinician. The location may be a particular area of a single healthcare facility or may be a particular healthcare facility among a plurality of healthcare facilities. For example, a clinician may have different roles depending on the particular unit within the healthcare facility the clinician is located. Or, the clinician may have different roles depending on the particular healthcare facility (that may be part of a related or commonly managed network of healthcare facilities) a clinician is making rounds.

At step 420, a workplace including one or more applications associated with the clinician and based on a location and role of the clinician are received from a server. The applications may be clinical or non-clinical as described above. Particular functionality or display of the applications may similarly be influenced by the location and role of the clinician. For example, some components of a particular application may be important to one role or location but not another. Accordingly, the components or functionality of a particular application may be limited or enhanced based on these considerations. This increases the efficiency associated with the computing infrastructure of the healthcare facility by providing applications or portions of applications only as needed or desired. The workplace is displayed on the first device at step 420.

In one embodiment, an indication is received that a second device received an authentication request from the clinician. The request signals to the server that the clinician desires to switch devices. In one embodiment, a session associated with the workspace on the first device is suspended. This allows the clinician to view the clinician's workspace in the same state, at the same point within an application or applications as it was on the first device when the session is resumed on the second device. In one embodiment, the workplace and session (i.e., session information) is communicated to the second device. Even though the session is resumed in the same state as it was on the first device, the workplace may include or exclude applications depending on what is appropriate for that location and the role associated with the clinician or for the particular device. For example, the clinician may be viewing the patient's EMR on a mobile device and also have an email application open. Although both applications are suspended, it would not be appropriate to include the email application in a workspace that is displayed on a particular device type or a particular location, such as an anchor device in a patient's room. Accordingly, only the patient's EMR is included in the workplace (and any other relevant clinical applications). In one embodiment, the session includes peripheral device information associated with the second device.

In one embodiment, an indication is received that the first device received an authentication request. As described above, this can occur automatically when a clinician exits a patient's room or is no longer proximate to a second device. In one embodiment, the workplace and session information is communicated to the first device. Continuing the above example, once the clinician transitions back to the mobile device, the email application is resumed in the clinician's workplace in the same state prior to transitioning from the mobile device to the anchor device.

Many different arrangements of the various components depicted, as well as components not shown, are possible without departing from the scope of the claims below. Embodiments of our technology have been described with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

The invention claimed is:

1. A method comprising:
    causing a computerized workspace for a particular user to be generated for display on a computing device at a physical location, wherein the computerized workspace includes an application that is specific to a role of the particular user and the physical location of the computing device;

receiving an indication when the computerized workspace for the particular user is initiated on another computing device at another physical location;

determining a particular graphical user interface of the application is displayed at the computing device at the physical location;

causing the computing device at the physical location to stop the application in the computerized workspace based on the indication received;

determining that the other physical location is associated with a privacy risk to the privacy of a patient; and causing the particular graphical user interface of the application to be generated for display in the computerized workspace on the other computing device at the other physical location with identifying information of the patient masked.

2. The method of claim 1, wherein causing the particular graphical user interface of the application to be generated for display in the computerized workspace on the other computing device at the other physical location includes automatically navigating to the particular graphical user interface of the application.

3. The method of claim 1, further comprising:
determining that the other physical location is outside of a room of the patient or a private office of the clinician to determine that the other physical location is associated with the privacy risk; and
when causing the particular graphical user interface of the application to be generated for display in the computerized workspace on the other computing device at the other physical location with the identifying information of the patient masked, masking the identifying information by at least partially obscuring patient identifying information from the particular graphical user interface to prevent display on the other computing device.

4. The method of claim 1, further comprising:
determining that the other physical location is outside of a room of the patient or a private office of the clinician to determine that the other physical location is associated with the privacy risk; and
when causing the particular graphical user interface of the application to be generated for display in the computerized workspace on the other computing device at the other physical location with the identifying information of the patient masked, masking the identifying information by at least partially removing patient identifying information from the particular graphical user interface to prevent display on the other computing device.

5. The method of claim 1, further comprising:
determining that the other physical location is outside of a room of the patient or a private office of the clinician to determine that the other physical location is associated with the privacy risk; and
when causing the particular graphical user interface of the application to be generated for display in the computerized workspace on the other computing device at the other physical location with the identifying information of the patient masked, masking the identifying information by at least partially hiding patient identifying information from the particular graphical user interface to prevent display on the other computing device.

6. The method of claim 1, wherein the other computing device utilizes a different operating system than the computing device, and wherein causing the particular graphical user interface of the application to be generated for display in the computerized workspace on the other computing device at the other physical location includes automatically navigating to the particular graphical user interface of the application as run by the different operating system.

7. The method of claim 1, wherein one or more of the computing device or the other computing device is a mobile computing device, wherein causing the particular graphical user interface of the application to be generated for display in the computerized workspace on the other computing device at the other physical location includes automatically navigating to the particular graphical user interface of the application as run in a mobile view.

8. One or more non-transitory computer storage media devices having computer-executable instructions embodied thereon for performing a method when executed by one or more processors, the media comprising:
causing a computerized workspace for a particular user to be generated for display on a computing device at a physical location, wherein the computerized workspace includes an application that is specific to a role of the particular user and the physical location of the computing device;
receiving an indication when the computerized workspace for the particular user is initiated on another computing device at another physical location;
determining a particular graphical user interface of the application is displayed at the computing device at the physical location;
causing the computing device at the physical location to stop the application in the computerized workspace based on the indication received;
determining that the other computing device is associated with a privacy risk to the privacy of a patient; and
causing the particular graphical user interface of the application to be generated for display in the computerized workspace on the other computing device at the other physical location with identifying information of the patient masked.

9. The media of claim 8, further comprises:
determining the particular graphical user interface of the application that is displayed at the computing device at the physical location is associated with an electronic record; and
wherein causing the particular graphical user interface of the application to be generated for display in the computerized workspace on the other computing device at the other physical location includes automatically loading information from the electronic record into the particular graphical user interface of the application.

10. The media of claim 8, further comprising:
determining that the other computing device is associated with the privacy risk by determining that the other computing device is shared by multiple users; and
in response to determining the other computing device is shared by multiple users, masking the identifying information by at least partially obscuring patient identifying information from the particular graphical user interface to prevent display on the other computing device when causing the particular graphical user interface of the application to be generated for display in the computerized workspace on the other computing device at the other physical location.

11. The media of claim 8, further comprising:
determining that the other computing device is associated with the privacy risk by determining that the other computing device is shared by multiple users; and
in response to determining the other computing device is shared by multiple users, masking the identifying information by at least partially removing patient identifying information from the particular graphical user interface to prevent display on the other computing device when causing the particular graphical user interface of the application to be generated for display in the computerized workspace on the other computing device at the other physical location.

12. The media of claim 8, further comprising:
determining that the other computing device is associated with the privacy risk by determining that the other computing device is shared by multiple users; and
in response to determining the other computing device is shared by multiple users, masking the identifying information by at least partially hiding patient identifying information from the particular graphical user interface to prevent display on the other computing device when causing the particular graphical user interface of the application to be generated for display in the computerized workspace on the other computing device at the other physical location.

13. The media of claim 8, wherein the other computing device utilizes a different operating system than the computing device, and wherein causing the particular graphical user interface of the application to be generated for display in the computerized workspace on the other computing device at the other physical location includes causing an automatic navigation to the particular graphical user interface of the application as run by the different operating system.

14. The media of claim 8, wherein one or more of the computing device or the other computing device is a mobile computing device, wherein causing the particular graphical user interface of the application to be generated for display in the computerized workspace on the other computing device at the other physical location includes causing an automatic navigation to the particular graphical user interface of the application as run in a mobile view.

15. A system comprising:
one or more processors configured to:
cause a computerized workspace for a particular user to be generated for display on a computing device at a physical location, wherein the computerized workspace includes an application that is specific to a role of the particular user and the physical location of the computing device;
receive an indication when the computerized workspace for the particular user is initiated on another computing device at another physical location;
determine a particular graphical user interface of the application 1s displayed at the computing device at the physical location;
cause the computing device at the physical location to stop the application in the computerized workspace based on the indication received;
determining that the other physical location is associated with a privacy risk to the privacy of a patient; and
cause the particular graphical user interface of the application to be generated for display in the computerized workspace on the other computing device at the other physical location with identifying information of the patient masked.

16. The system of claim 15, wherein causing the particular graphical user interface of the application to be generated for display in the computerized workspace on the other computing device at the other physical location includes automatically navigating to the particular graphical user interface of the application.

17. The system of claim 15, further comprising:
determining that the other physical location is outside of a room of the patient to determine that the other physical location is associated with the privacy risk; and
when causing the particular graphical user interface of the application to be generated for display in the computerized workspace on the other computing device at the other physical location with the identifying information of the patient masked, masking the identifying information by at least partially obscuring patient identifying information from the particular graphical user interface to prevent display on the other computing device.

18. The system of claim 15, further comprising:
determining that the other physical location is outside of a private office of the clinician to determine that the other physical location is associated with the privacy risk; and
when causing the particular graphical user interface of the application to be generated for display in the computerized workspace on the other computing device at the other physical location with the identifying information of the patient masked, masking the identifying information by at least partially removing patient identifying information from the particular graphical user interface to prevent display on the other computing device.

19. The system of claim 15, further comprising:
determining that the other physical location is outside of a room of the patient or a private office of the clinician to determine that the other physical location is associated with the privacy risk; and
when causing the particular graphical user interface of the application to be generated for display in the computerized workspace on the other computing device at the other physical location with the identifying information of the patient masked, masking the identifying information by at least partially hiding patient identifying information from the particular graphical user interface to prevent display on the other computing device.

20. The system of claim 15, wherein the other computing device utilizes a different operating system than the computing device, and wherein causing the particular graphical user interface of the application to be generated for display in the computerized workspace on the other computing device at the other physical location includes automatically navigating to the particular graphical user interface of the application as run by the different operating system.

* * * * *